US00PP21012P2

(12) United States Plant Patent
Hofmann

(10) Patent No.: US PP21,012 P2
(45) Date of Patent: May 25, 2010

(54) **NEW GUINEA *IMPATIENS* PLANT NAMED 'FISNICS SWEPU'**

(50) Latin Name: *Impatiens hawkeri*
Varietal Denomination: Fisnics Swepu

(75) Inventor: Birgit Christa Hofmann, Ruedesheim (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/383,040

(22) Filed: Mar. 19, 2009

(51) Int. Cl.
*A01H 5/00* (2006.01)

(52) U.S. Cl. ..... Plt./318.1

(58) Field of Classification Search ..... Plt./318.1
See application file for complete search history.

*Primary Examiner*—Susan B McCormick Ewoldt
(74) *Attorney, Agent, or Firm*—S. Matthew Edwards

(57) ABSTRACT

A New Guinea *Impatiens* plant named 'Fisnics Swepu,' particularly distinguished by red-purple and light lavender, bi-color flower color, glossy, dark green foliage, dense and fairly compact habit, small to medium plant size, and about mid season start of flowering.

1 Drawing Sheet

Latin name of the genus and species of the plant claimed: *Impatiens hawkeri.*

Varietal denomination: 'Fisnics Swepu'.

BACKGROUND OF THE NEW PLANT

The present invention comprises a New Guinea *Impatiens*, botanically known as *Impatiens hawkeri* and hereinafter referred to by the variety name 'Fisnics Swepu'.

'Fisnics Swepu' is a product of a planned breeding program. The new cultivar has bluish pink and deep red, bi-color flowers, dark green foliage and a relatively tight, medium sized habit.

'Fisnics Swepu' originated from a hybridization made in the summer of 2004 in a controlled breeding program in Hillscheid, Germany. The female parent was an unpatented hybrid seedling identified as 'K03-2664-4,' with large flowers with deep cherry-red pattern on deep pink ground color, and a small plant habit.

The male parent of 'Fisnics Swepu' was an unpatented hybrid seedling, identified as 'K04-4115-2,' with bi-color flowers showing a red-purple star-shaped pattern on light lavender ground color, with large, medium green leaves and a small to medium sized plant habit.

'Fisnics Swepu' was selected as one flowering plant within the progeny of the stated cross in the spring of 2005 in a controlled environment in Moncarapacho, Portugal.

The first act of asexual reproduction of 'Fisnics Swepu' was accomplished when vegetative cuttings were taken from the initial selection in July 2005 in a controlled environment in Moncarapacho, Portugal.

Horticultural examination of plants grown from cuttings of the plant initiated in the February of 2006 in Hillscheid, Germany, and continuing thereafter, has demonstrated that the combination of characteristics as herein disclosed for 'Fisnics Swepu' are firmly fixed and are retained through successive generations of asexual reproduction.

'Fisnics Swepu' has not been observed under all possible environmental conditions. The phenotype may vary significantly with variations in environment such as temperature, light intensity and day length.

Plant Breeder's Rights for this cultivar were applied for in Canada on Apr. 29, 2008 and in Switzerland on Mar. 20, 2008. 'Fisnics Swepu' has not been made publicly available more than one year prior to the filing of this application.

BRIEF DESCRIPTION OF DRAWING

The accompanying photographic drawing shows typical flower and foliage characteristics of 'Fisnics Swepu' with colors being as true as possible with an illustration of this type. The photographic drawing shows a flowering potted plant of the new variety.

DETAILED BOTANICAL DESCRIPTION

The measurements were taken in Hillscheid, Germany, in late August 2008 on about 6 month old plants that were growing outdoors. Culture of these plants had started in late February 2008 when rooted cuttings were planted into 12 cm pots, placed in the greenhouse and cultivated at a minimum temperature of 16° C. In late May plants were transplanted, 3 each, into 45 cm diameter containers that were placed outdoors, two containers per variety were placed along the greenhouse under rain protection.

Color Chart used: Royal Horticultural Society Colour Chart (R.H.S.) 2001.

BRIEF SUMMARY OF INVENTION

The following observations, measurements, and comparisons describe plants grown indoors and outdoors in Hillscheid, Germany, and Chatelerault, France. The following traits have been repeatedly observed and are determined to be basic characteristics of the new variety. The combination of these characteristics distinguishes this New Guinea *Impatiens* as a new and distinct variety.

1. Red-purple and light lavender, bi-color flower color.
2. Large, somewhat zygomorphic flowers.
3. Dark green, glossy foliage, elliptically shaped leaves.
4. About medium vigor, compact to medium sized.
5. Mounded, semi-spherically shaped, and relatively tight plant habit.
6. About mid season flowering response.

DIFFERENCES BETWEEN THE NEW VARIETY 'FISNICS SWEPU' AND SIMILAR VARIETIES

In comparison with 'Fisnics Pursweet,' U.S. Plant Pat. No. 17,692, 'Fisnics Swepu' has somewhat larger flowers, petals showing a stronger contrast of the two colors, and somewhat tighter and a little more compact plant habit.

In comparison to 'Spixis,' U.S. application No. 08/797,866 (applied as 'Kispix'), abandoned, 'Fisnics Swepu' has somewhat larger flowers, a deeper red and more distinct red pattern on petals, and a more compact plant habit.

In comparison to 'Guadeloupe Improved,' synonym 'Paradise Fuchsia on Lavender,' U.S. Plant Pat. No. 10,429 (patented as 'Kimpgua'), 'Fisnics Swepu' has a more red-purple, less violet, overall flower color, distinctly larger flowers, and dark green foliage, while 'Kimpgua' has medium green leaves.

Plant:
- *Form, growth and habit.*—Mounding, semi-spherical shape, relatively tight, well-branching.
- *Plant height.*—22–25 cm.
- *Plant width.*—28–35 cm.
- *Number of branches.*—10–15.
- *Propagation.*—Terminal tips for cuttings.
- *Time to initiate and develop roots.*—18 days or less at 22° C.
- *Time to produce a finished flowering plant.*—About 10 weeks for a 12 cm pot.

Stem:
- *Color of stem.*—RHS 146D, near the nodes brownish, about RHS 184A or lighter.
- *Length of stem.*—Approximately 20–28 cm.
- *Diameter.*—0.7–0.9 cm.
- *Length of internodes.*—3–6 cm.
- *Texture.*—Glabrous.

Foliage:
- *Arrangement.*—Mainly in whorls.
- *Growing leaf, color upper surface.*—RHS 147A.
- *Growing leaf, lower surface.*—RHS 187C.
- *Mature leaf, color upper surface.*—Near RHS 139A, or deeper than RHS 147A.
- *Mature leaf, color lower surface.*—RHS 183A or 187C to 187D.
- *Length.*—11.0–12.0 cm.
- *Width.*—4.0–4.5 cm.
- *Shape.*—Elliptical.
- *Base shape.*—Acute.
- *Apex shape.*—Acuminate.
- *Margin.*—Slightly serrate, ciliate.
- *Texture.*—Leathery, glossy, smooth to somewhat rugose.
- *Color of veins, upper surface.*—Reddish, RHS 53B.
- *Color of veins, lower surface.*—RHS 60A.

Petiole:
- *Color upper surface.*—RHS 53B to 53C.
- *Color lower surface: RHS* 60A.
- *Length.*—About 1.0–2.0 cm.
- *Diameter.*—3–4 mm.
- *Texture.*—Mainly glabrous.

Inflorescence:
- *Duration of flowering.*—Continuous flowering from spring through fall, in the greenhouse possibly year round depending on light intensity.
- *Blooming habit, start.*—9 weeks after planting of rooted cuttings.
- *Inflorescence type.*—Flowers appear solitary in the leaf axils of the upper nodes of the stems.
- *Number of flowers per node.*—About 4–8 open flowers and buds in various stages of development.
- *Number of flowers per plant.*—15–17.
- *Lastingness of individual blooms.*—Up 9–12 days (18° C., greenhouse in springtime).

Pedicel:
- *Color of pedicel.*—RHS 144B to 144C.
- *Length of pedicel.*—5.0–5.3 cm.
- *Diameter of pedicel.*—1 mm.
- *Texture.*—Glabrous, flexible.

Flower:
- *Form.*—Single-type, 5 petals.
- *Shape of corolla.*—Slightly zygomorphic, nearly flat, with the petals partly overlapping.
- *Overall color.*—Bi-color: lavender ground color, and strong red-purple pattern, star-shaped and with a large splotch on upper petal.
- *Main/ground color, upper surface.*—RHS N74C to N74D, may fade to 75A.
- *2nd color, markings.*—RHS N66A.
- *Lower surface.*—RHS 58B–58C.
- *Length of flower.*—7.8–8.0 cm.
- *Width of flower.*—7.5—7.8 cm.
- *Depth of flower.*—1.0–1.5 cm.

Petals:
- *Shape of banner petal.*—Obcordate.
- *Lateral and lower petals.*—Obovate.
- *Apex shape.*—Emarginate.
- *Base.*—Attenuate.
- *Margin.*—Entire.

Petal size:
- *Upper (banner) petal, length.*—3.4–3.6 cm.
- *Upper petal, width.*—5.1–5.3 cm.
- *Lateral petals, length.*—3.5–3.7 cm.
- *Lateral petals, width.*—3.3–3.6 cm.
- *Lower petals, length.*—3.6–3.8 cm.
- *Lower petals, width.*—4.0–4.2 cm.

Spur:
- *Position and shape.*—Elongate, curving downwardly.
- *Color.*—Cream, RHS 159A to pale green, RHS 145C.
- *Length.*—Most often 6.5 cm.
- *Diameter.*—3 mm.

Bud (just before opening):
- *Shape.*—Ovoid.
- *Length.*—2.1 cm.
- *Diameter.*—1.5 cm.

Calyx:
- *Number of sepals.*—4–5, the upper one fused with the underside of the banner petal, 2 lateral sepals, and a large sepal (2 fused sepals) bearing the spur.
- *Color of lateral sepals.*—RHS 180D.
- *Shape of lateral sepals.*—Ovoid with acute tip.
- *Length of lateral sepals.*—1.3–1.6 cm.
- *Width of lateral sepals.*—0.6–0.7 cm.
- *Color of large sepal.*—RHS 56B.
- *Shape of large sepal.*—Ovate to elliptical with cuspidate tip.
- *Length of large sepal.*—1.9 cm.
- *Width of large sepal.*—1.7 cm.
- *Margins.*—Entire.
- *Texture.*—Glabrous.

Reproductive organs:
- *Pistil.*—One per flower.
- *Length.*—0.6–0.7 cm.
- *Ovary shape.*—Elongate, 5-celled.
- *Color of ovary.*—Brown, RHS 187B.

*Style and stigma.*—Very short, purple-pink color, RHS 60D.

*Androeceum.*—5 stamen, fused, the anthers hooded.

*Diameter.*—5–6 mm.

*Surface color.*—Weak pink, RHS N66C.

*Pollen amount.*—Moderate.

*Color of pollen.*—RHS 8D (whitish-yellow).

*Fertility/seed set.*—No seed set observed.

Disease/pest resistance: Disease resistance or susceptibility has not been observed on this hybrid.

What is claimed is:

1. A new and distinct variety of New Guinea *Impatiens* plant named 'Fisnics Swepu,' substantially as illustrated and described herein.

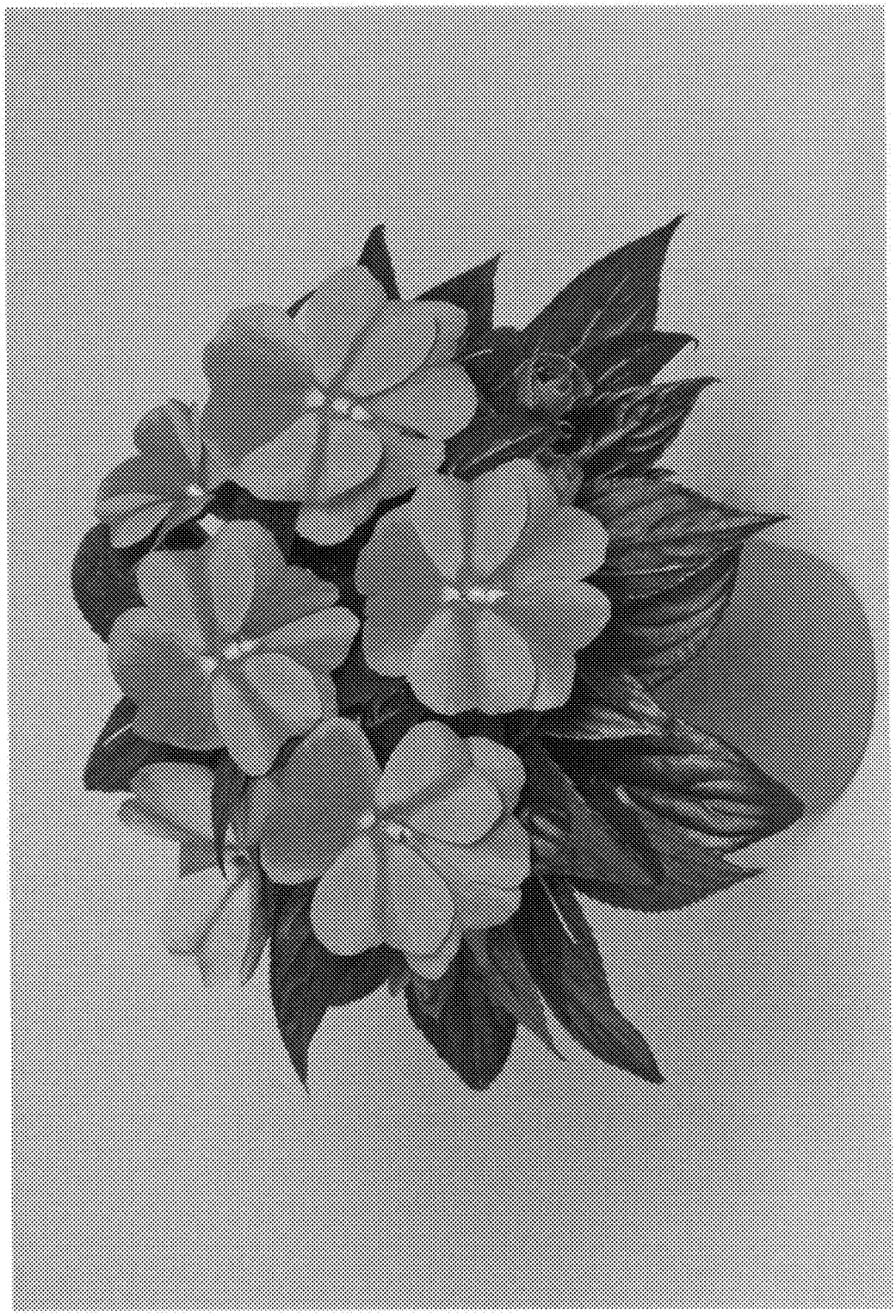

* * * * *